(12) United States Patent
Groß et al.

(10) Patent No.: US 7,972,061 B2
(45) Date of Patent: Jul. 5, 2011

(54) C-ARM HAVING A RADIOGRAPHIC SOURCE AND A HEAT PUMP

(75) Inventors: Stefan Groβ, Trabitz (DE); Dieter Heinl, Erbendorf (DE); Frank Rosinus, Wolfen (DE)

(73) Assignee: Siemens Aktiengesellschaft, Munich (DE)

( * ) Notice: Subject to any disclaimer, the term of this patent is extended or adjusted under 35 U.S.C. 154(b) by 69 days.

(21) Appl. No.: 12/346,170

(22) Filed: Dec. 30, 2008

(65) Prior Publication Data

US 2009/0175421 A1   Jul. 9, 2009

(30) Foreign Application Priority Data

Jan. 3, 2008   (DE) .......................... 10 2008 003 088

(51) Int. Cl.
*H05G 1/02*   (2006.01)
(52) U.S. Cl. ........................................ 378/197; 378/199

(58) Field of Classification Search .................. 378/193, 378/197, 198, 199, 200
See application file for complete search history.

(56) References Cited

U.S. PATENT DOCUMENTS

2008/0304625 A1 *  12/2008  Dehler et al. ................. 378/197

FOREIGN PATENT DOCUMENTS

DE    10 2007 026 677 A1   12/2008

OTHER PUBLICATIONS

German Office Action dated Jan. 22, 2009 with English translation.

* cited by examiner

*Primary Examiner* — Jurie Yun
(74) *Attorney, Agent, or Firm* — Lempia Summerfield Katz LLC

(57) ABSTRACT

An x-ray device is provided. The x-ray device includes a C-arm, on which a radiographic source and a heat pump are arranged. At least sections of the C-arm are hollow, such that at least sections of the radiographic source and the heat pump are arranged inside the C-arm.

14 Claims, 3 Drawing Sheets

C-ARM HAVING A RADIOGRAPHIC SOURCE AND A HEAT PUMP

The present patent document claims the benefit of German Patent Application No. DE 10 2008 003 088.0, filed on Jan. 3, 2008, which is hereby incorporated by reference.

BACKGROUND

The present embodiments relate to an x-ray device include a C-arm having a radiographic source and a heat pump.

An x-ray device may include a C-arm that is able to be rotated via a rotation guide around a normally horizontally-aligned axis on a floor-mounted stand. The rotation guide of the C-arm is able to be rotated along its arc-shaped guidance track around an isocenter. When the C-arm is moved at significant speed along the rotation guide, a light C-arm should be used to achieve the best possible dynamics. An angiography x-ray device is one example where the C-arm may be moved at significant speed along the rotation guide. Accordingly, C-arms made from extruded profiles are normally used which exhibit a hollow cross-sectional profile.

Instead of a floor stand and the linkage of the C-arm via the rotation guide, via which elements the required degree of freedom of movement for the C-arm movement and positioning are implemented, the practice is known of arranging the C arm on an industrial robot with a robot arm and a corresponding control device. In such an embodiment the degrees of freedom needed are guaranteed by the six axes of movement of the robot in connection with a rotational mounting of the C-arm on the robot arm. The C-arm is mounted to allow direct rotation on the robot arm in such cases.

X-ray devices may include a radiographic source along with heat pump placed on the end of the C-arm. In other words, the heat pump is attached to the inside of the arm and projects inwards. After a diaphragm has been placed on the radiographic source, the entire assembly extends a significant distance into the inside of the arc in the direction of the radiation detector. To attach radiographic source, the radiographic source is usually screwed to the C-arm with round brackets, after which the diaphragm is fitted. The radiographic source can lie across the arm or along the arm. Different types of diaphragm can be fitted.

As a result of this arrangement and of the resulting structure protruding far into the inside of the arc, problems can occur in operation of positioning the C-arm or the radiographic source respectively for the appropriate recording of a specific image. The tall structure can greatly restrict the freedom of movement and the opportunity for positioning, for example, when the patient bed is to be moved downwards or an image is to be recorded at a wide angle. Accordingly, the tall structure can easily collide with the patient bed or other peripheral devices, for example, or can come close to the devices, which restricts its movement.

An installation of the heat pump would be difficult in such cases.

SUMMARY AND DESCRIPTION

The present embodiments may obviate one or more of the problems inherent in the related art. For example, in one embodiment, an x-ray device allows an improved positioning of the C-arm.

In one embodiment, an x-ray device includes at least some parts of the radiographic source and the heat pump being arranged inside the C-arm of which at least some sections are hollow.

The radiographic source and the heat pump may be arranged at least partly or if possible almost completely recessed into the inside of the C-arm. At least sections of the C-arm are hollow and accessible. The recessed arrangement integrated into the C-arm leads to the radiographic source protruding far less or not at all from the C-arm geometry, so that only the diaphragm placed over it projects into the inside of the arc in the direction of the isocenter. Accordingly, the height of this entire assembly may be reduced. The C-arm end may be significantly narrower and may be used in more confined areas than was previously possible. In other words, the C-arm may be below a patient bed, for example, or is able to be set at an even greater angle without colliding with the patient bed. The positioning options and the imaging opportunities are significantly improved in this way.

In one embodiment, the radiographic source and the heat pump may be inserted into a support frame forming a part of the C-arm, which is fitted detachably to one end of the C-arm, lengthening the latter. Accordingly, the assembly may be mounted in advance. The radiographic source and heat pump may be attached to the support frame and then the entire assembly may be attached to the end of the C-arm. Some sections of the heat pump, which, when the radiographic source is fitted longitudinally, arranged in front of this, will usually project slightly from the support frame, are inserted into the hollow C-arm section.

Since the radiographic source and the heat pump are parts subject to wear, which have to be exchanged or serviced, disassembly is very easy. The support frame may be released from the end of the C-arm, after which this entire radiation source assembly can be removed. The exchange of the radiographic source and/or the heat pump is then easily possible on the disassembled support frame. Re-assembly is designed to be just as easy, the support frame only has to be connected to the end of the C-arm again and the corresponding supply lines connected to the heat pump or the radiographic source respectively, after which the entire device is the immediately ready to operate again. A mechanical interface is thus provided here on or within the arm respectively, enabling easy assembly and disassembly of the entire preconfigurable radiation source assembly comprising radiographic source, heat pump and naturally the corresponding control electronics (usually a small control board).

In one embodiment, flange-type attachment elements are provided on the end faces of the support frame and on the C-arm. The flange-type attachment elements may be used for attaching the support frame to the C-arm. The attachment elements may be, for example, screws. The attachment elements may be used to attach the support frame to the C-arm. This makes fast and simple assembly and disassembly possible.

In one embodiment, the radiographic source may be attached to the support frame via an adjustable attachment, which allows adjustment. The radiographic source may be adjusted directly on the support frame. If, for example, the heat pump has to be replaced, the support frame together with the adjusted radiographic source and the heat pump attached to the support frame may be disassembled, after which only the heat pump is replaced. The radiographic source is not disassembled. The radiographic source remains in the adjusted position. Complex adjustment processes are advantageously dispensed with here if the radiation source assembly itself is not affected by the replacement or the overhaul. This offers a further significant advantage compared to previously known systems, in which usually the radiation source assembly also has to be disassembled in the event of the heat pump being serviced or replaced, resulting in a renewed adjustment process.

Coolant lines routed to the heat pump may be disposed on or in the C-arm. Accordingly, the heat pump may be coupled via suitable connections in the form of hydraulic quick-release couplings to connections provided on the heat pump. The connections provided on the coolant lines and the heat pump are self-sealing, hydraulic, quick-release couplings, which allow the connections to be made and released quickly, but simultaneously to make sure that no coolant escapes either during connection or during disconnection. This is important in order to avoid contamination during assembly or disassembly of the radiation source assembly mounted on the support frame.

An electronics unit may be used to control the radiographic source, which is detachably connected via one or more connections to one or more lines routed on or in the C-arm may be provided on the support frame. The entire radiation source assembly comprising radiographic source, heat pump and control electronics is arranged as a prefabricated module on the support frame and only the corresponding supply or control lines, such as coolant lines, electricity supply lines, and the control lines for the electronics need to be connected, which can be done very quickly and easily.

These supply or control lines may be routed to the support frame either running along the outside of the C-arm or the supply or control line can run inside the hollow C-arm, which may have a structure open on at least one access side, for example, accessible from this side. The supply or control lines and the other components used for operation of the radiographic source and the radiographic detector located at the other end of the arm may be arranged inside the arm. Accordingly, a C-arm may be used in conjunction with an industrial robot, via which the C-arm can be controlled in its overall spatial movement. Regardless of the use of the C-arm, the use of the support frame, the implementation of the additional, especially mechanical interface on the C-arm is advantageous.

The support frame may include one or more detachably arranged cladding elements on the support frame. The support frame, which is open on as many sides as possible to allow a simple mechanical connection of the radiographic source with the frame, may be closed off via the one or more detachably arranged cladding elements.

DETAILED DESCRIPTION

Figure 1:
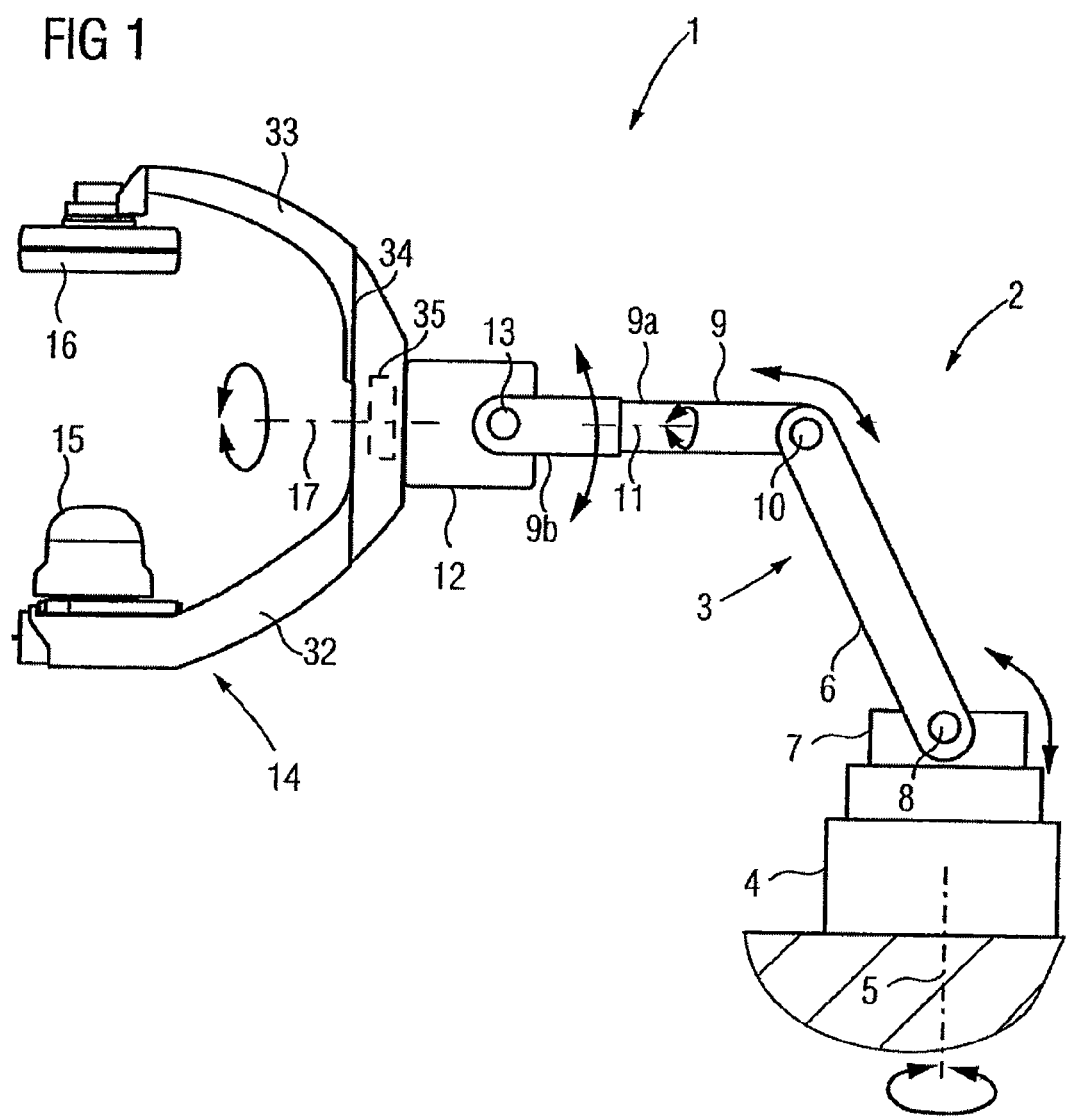
FIG. 1 a basic diagram of an inventive x-ray device comprising an industrial robot, on which the C-arm which supports the radiographic source is arranged.

FIG. 1 shows an x-ray device 1 including an industrial robot 2, with a robotic arm 3. The industrial robot 2 is accommodated on a base 4, which is arranged on the floor side in FIG. 1. The robotic arm 3 may be rotated overall on the base 4 around a vertical axis 5. The industrial robot 2 is supported on the base 4 via a first robotic arm 6 on a base section 7 able to be rotated around the vertical axis, on which it is additionally able to be pivoted around a horizontal axis 8. Located on the first robotic arm 6 is a second robotic arm 9, which is able to be pivoted on the first robotic arm 6 around a second horizontal axis 10. The second robotic arm 9 includes the first arm section 9a, which is arranged on the first robotic arm 6, as well as a second arm section 9b, which is able to rotate around a further axis 11 relative to the arm section 9a. A C-arm mount 12, which is disposed on the second arm section 9b, is able to be rotated around the axis 13. The C-arm 14, on which are arranged a radiographic source 15 as well as a radiographic detector 16, is able to be rotated on the C-arm mount 12 around a further axis of rotation 17. Accordingly, the x-ray device 1 may be a 6-axis system, which allows a free movement of the C-arm 14 in space.

Figure 2:
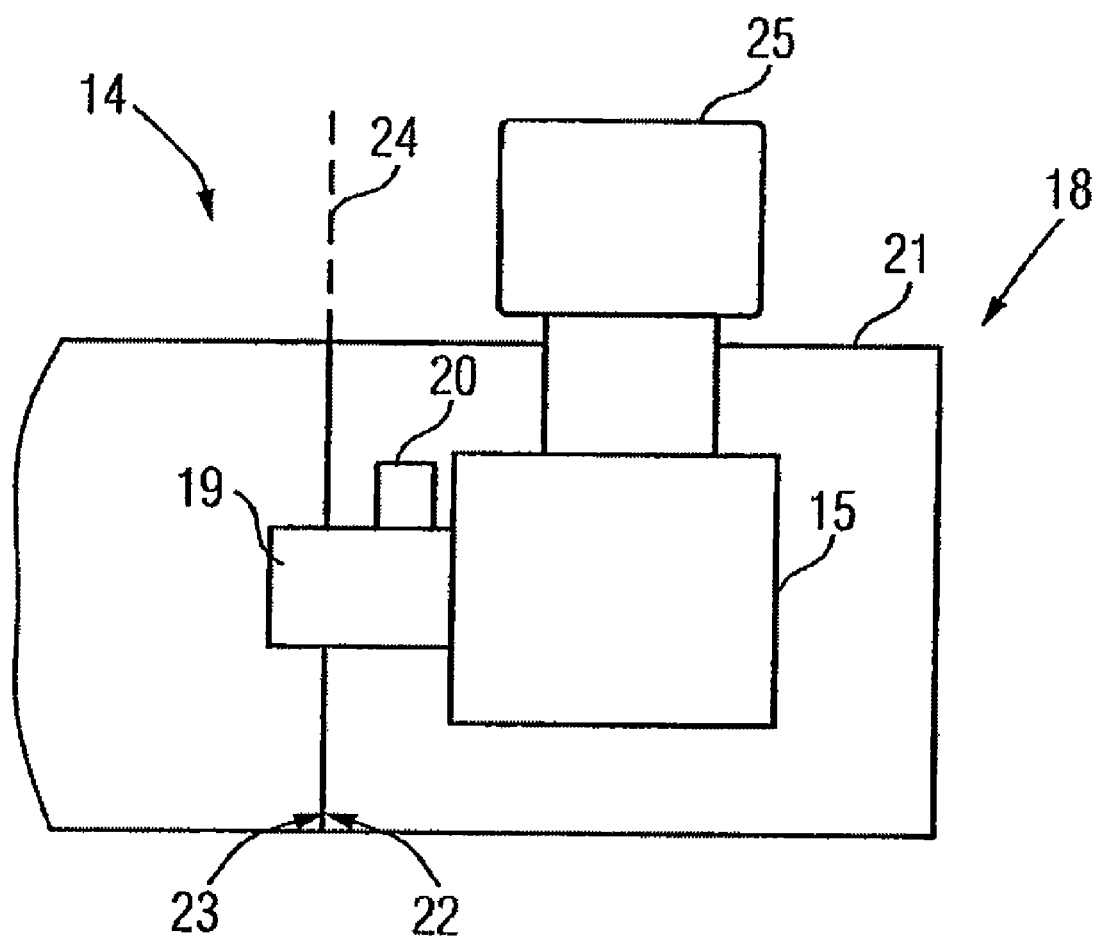
FIG. 2 a basic diagram relating to the arrangement of the radiographic source together with the heat pump and control electronics inside the C-arm or inside a support frame disposed on said C-arm, and FIG. 3 a part view of a practical embodiment of such a support frame with integrated radiographic source and heat pump.

FIG. 2 shows as a C-arm 14. The C-arm 14 is extended by a module 18 including the radiographic source 15, a heat pump 19 assigned to the radiographic source 15, and an electronic unit 20 operating or controlling the heat pump 19 and/or the radiographic source 15. These components (radiographic source 15, heat pump 19, electronic unit 20) are arranged on or respectively in a support frame 21, which is attached detachably by the front side via a corresponding flange-type attachment section 22 to the front side of the C-arm 14, which likewise includes a flange-like attachment section 23. A mechanical interface 24, as shown by the dashed line in FIG. 2, is thus realized. The support frame 21 with the components (radiographic source 15, heat pump 19, electronic unit 20) built into it or onto it forms a separate, preconfigured unit. The preconfigured unit may be flanged onto the C-arm 14 in a quick and simple manner, with the support frame 21 then forming a part of the C-arm 14 and extending the C-arm 14, so that overall the radiographic source 15 along with heat pump 19 and the electronic unit 20 are arranged integrated into the C-arm 14. As shown in FIG. 2, a diaphragm 25 may sit on the support frame 21 and may be positioned downstream from the radiographic source 15. The diaphragm 25 may solely define how far the entire module is raised towards the center of the C-arm 14, for example, projects inwards in the direction of the radiographic detector.

Figure 3:
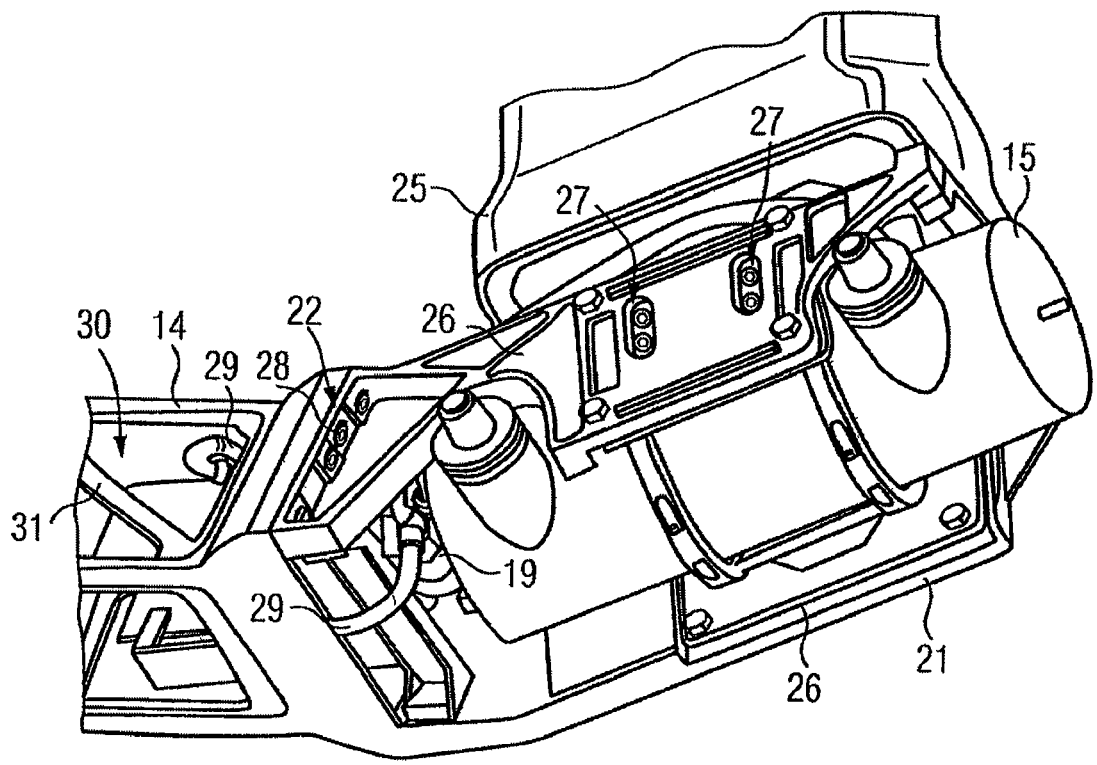

FIG. 3 shows one exemplary embodiment of a mounting frame 21 together with integrated radiographic source 15 and heat pump 19 as well as the electronic unit 20. The support frame 21 is a component open on the lower and upper side as well as the front side. The support frame 21 may be a metal casting. Corresponding attachment sections are provided at the sides 26 in order to fix the radiographic source 15 via corresponding attachment elements 27 to the support frame 21. The attachment elements 27, such as screws, are designed so that in conjunction with corresponding attachment points on the radiographic source 15 they allow adjustment of the radiographic source 15 relative to the support frame 21. The position of the radiographic source 15 on the support frame 21 may be set accordingly and subsequently permanently fixed. Connected downstream from the radiographic source 15 is the heat pump 19, which is attached to the radiographic source 15. As shown FIG. 2, the radiographic source 15 projects slightly from the support frame 21. The radiographic source 15 may extend via the plane of intersection into the hollow C-arm 14. Provided on the end face side of the support frame 21 facing the C-arm 14 is a corresponding flange-like attachment section 22, in a corresponding manner such a flange-like attachment section 23 is provided on the end face side of the C-arm 14. The attachment is undertaken via attachment screws 28, which are easily accessible even when the radiographic source 15 and integrated heat pump 19 are inserted.

Routed through the C-arm are the corresponding supply lines and control lines to the heat pump 19, the radiographic source 15 and to the electronic unit 20. Shown as examples are two coolant lines 29 leading to the heat pump 19. The coolant lines 29 and the heat pump 19 have corresponding hydraulic quick-release couplings which are self sealing, so that the subsequent release of the cooling lines 29 at the heat pump 19 can take place very quickly and without any coolant escaping. Control lines not shown in any greater detail, which are connected to the electronic unit not shown in any greater detail, are likewise fed within the C-arm 14 to the support frame 21 and can be readily connected via corresponding simple connectors to the electronic unit 20. The same applies to the electrical supply lines which are routed inside the C-arm 14 to the radiographic source 15, where they can be connected to the radiographic source 15.

As part of the installation, the radiographic source 15, the heat pump 19, and the electronic unit 20 may be initially arranged on the support frame side, so that overall a prefabricated assembly is produced, which is only subsequently married (attached) to the remainder of the C-arm 14. The support frame may then be secured to the C-arm 14 by screws 28 with the heat pump 19 extending slightly into the arm. The diaphragm 25 is then fitted, but this can also be done before it is screwed to the C-arm. The coolant lines 29 or the control lines and the electrical supply lines may be plugged into the corresponding components, after which the entire unit is enclosed by corresponding cladding elements.

Disassembly in the event of the radiation source assembly 15 or the heat pump 19 having to be maintained or repaired is a correspondingly simple process. Only the cladding elements have to be removed, after which the attachment screws 28 are released and the support frame 21, complete with the module, is pulled away from the end face of the C-arm 14. The heat pump may be easily accessible and can be disassembled without the adjustment of the radiation source assembly 15 having to be initiated via the attachment elements 27. The adjustment of the radiographic source 15 is not changed either during disassembly of the support frame 21 or during disassembly of the heat pump 19. The radiation source 15 maintains this aligned adjusted position even if the support frame is fitted and removed a number of times.

As shown in FIG. 3, the C-arm may be a hollow component, which is open from at least one access side 30, where it can be enclosed using suitable cladding elements. Using a framework-type structure comprising a number of struts 31 running in the form of a framework, of which one is shown here in section, the appropriate mechanical stiffness is obtained on this open side. This open structure (the opposite side can also be designed with this framework-type tie-rod structure and be embodied as the access side) makes it possible to also integrate further electronic components used for the operation of the radiographic source 15 or (see FIG. 1) of the radiation detector 16 in the interior of the C-arm 14. All electronic components for an application of this system in connection with a robotic arm 3 may be accommodated inside the C-arm.

The C-arm, as depicted in FIG. 1, may include two sections 32 and 33. Section 33 may be guided on a linear guide 34 to allow linear movement on the first arm section 32. The first arm section 32 may be attached on a rotatable support to the robotic arm 3. The movement of arm section 33 and thereby of the detector 16 relative to the radiographic source 15 may be realized by a lifting device 35, likewise arranged inside the C-arm, here inside the arm section 32. The lift device 35, for example, comprises a drive motor with secondary gear and a fixed-position toothed wheel driven by the drive motor. The drive motor meshes with a toothed bar which is arranged on the second arm section 33. The linear movement can readily be realized mechanically in this way. In an alternative embodiment, the lift device 35 may include a spindle drive or a hydraulic, pneumatic or electrically-controllable positioning cylinder.

The invention claimed is:

1. An x-ray device comprising:
a radiographic source;
a heat pump; and
a C-arm having a C-arm end surface and a hollow section, the radiographic source and the heat pump being arranged at least partly in the interior of the hollow section of the C-arm,
wherein the radiographic source and the heat pump are inserted into a support frame forming at least a part of the C-arm, the support frame having a frame end surface facing the C-arm end surface, the frame end surface being detachably fixed to the C-arm end surface, the support frame lengthening the C-arm, and
wherein the support frame includes an opening at a side of the support frame.

2. The x-ray device as claimed in claim 1, further comprising flange-type attachment sections that are provided on the support frame and on the C-arm, the flange-type attachment section on the support frame comprising the frame end surface, and the flange-type attachment section on the C-arm comprising the C-arm end surface, the flange-type attachment sections being used to attach the support frame to the C-arm with fastening elements.

3. The x-ray device as claimed in claim 2, wherein the radiographic source is attached to the support frame via an adjustable attachment that permits adjustment.

4. The x-ray device as claimed in claim 2, further comprising coolant lines routed on or in the C-arm to the heat pump, the coolant lines being operable to be connected by detachable connections provided on the heat pump, detachable connections on the coolant lines and the detachable connections on the heat pump being self-sealing, quick-release couplings.

5. The x-ray device as claimed in claim 2, further comprising an electronics unit that controls the radiographic source, the heat pump, or the radiographic source and the heat pump, the electronics unit being provided in the support frame, the electronics unit being connected detachably via one or more connections to one or more lines routed on or in the C-arm.

6. The x-ray device as claimed in claim 1, wherein the radiographic source is attached to the support frame via an adjustable attachment that permits adjustment.

7. The x-ray device as claimed in claim 6, further comprising flange-type attachment sections that are provided on the support frame and on the C-arm, the flange-type attachment section on the support frame comprising the frame end surface, and the flange-type attachment section on the C-arm comprising the C-arm end surface, the flange-type attachment sections being used to attach the support frame to the C-arm with fastening elements.

8. The x-ray device as claimed in claim 6, further comprising coolant lines routed on or in the C-arm to the heat pump, the coolant lines being operable to be connected by detachable connections provided on the heat pump, detachable connections on the coolant lines and the detachable connections on the heat pump being self-sealing, quick-release couplings.

9. The x-ray device as claimed in claim 6, further comprising an electronics unit that controls the radiographic source, the heat pump, or the radiographic source and the heat pump, the electronics unit being provided in the support frame, the electronics unit being connected detachably via one or more connections to one or more lines routed on or in the C-arm.

10. The x-ray device as claimed in claim 1, further comprising coolant lines routed on or in the C-arm to the heat pump, the coolant lines being operable to be connected by detachable connections provided on the heat pump, detachable connections on the coolant lines and the detachable connections on the heat pump being self-sealing, quick-release couplings.

11. The x-ray device as claimed in claim 10, further comprising an electronics unit that controls the radiographic source, the heat pump, or the radiographic source and the heat pump, the electronics unit being provided in the support frame, the electronics unit being connected detachably via one or more connections to one or more lines routed on or in the C-arm.

12. The x-ray device as claimed in claim 1, further comprising an electronics unit that controls the radiographic source, the heat pump, or the radiographic source and the heat pump, the electronics unit being provided in the support frame, the electronics unit being connected detachably via one or more connections to one or more lines routed on or in the C-arm.

13. The x-ray device as claimed in claim 1, further comprising one or more detachably arranged cladding elements provided on the support frame.

14. The x-ray device as claimed in claim 13, wherein the one or more detachably arranged cladding elements are operable to close one or more openings in the support frame.

* * * * *